United States Patent [19]
Tamler et al.

[11] 4,308,012
[45] Dec. 29, 1981

[54] DENTAL PULP VITALITY TESTER

[76] Inventors: Richard Tamler, 2686 Sacramento St., San Francisco, Calif. 94115; Edward B. Stoneham, 3574 Aaron Dr., Santa Rosa, Calif. 95404

[21] Appl. No.: 114,037

[22] Filed: Jan. 21, 1980

[51] Int. Cl.³ .................................................. A61C 00/00
[52] U.S. Cl. .......................................... 433/32; 128/741
[58] Field of Search ............... 128/741, 742, 776, 777, 128/787, 800, 801; 433/27, 32; 62/3

[56] References Cited
U.S. PATENT DOCUMENTS 3,533,397  5/1966  Scher ......................................... 62/3
3,618,590  6/1969  Frank ......................................... 62/3
4,197,641  4/1980  Paulke ...................................... 433/32

Primary Examiner—Robert Peshock
Attorney, Agent, or Firm—Townsend and Townsend

[57] ABSTRACT

A dental pulp vitality tester for selectively applying heat, cold, or electrical stimulation to a patient's tooth in a controlled reproducible manner. Broadly, the device includes a handle having a thermally and electrically conductive probe tip, a heat sink within the handle, and a thermoelectric element having a first junction thermally coupled to the probe tip and a second junction thermally coupled to the heat sink. Heating or cooling of the probe tip is accomplished by passage of electric current through the thermoelectric element. A temperature sensing device such as a thermistor is thermally coupled to the probe tip, and temperature regulation circuitry responsive to the state of the temperature sensing element regulates the current to the thermoelectric element to maintain the temperature of the probe tip constant at a predetermined desired value. The present invention includes circuitry for quantifying the stimulus applied. In particular, circuitry is provided for sensing electrical contact with the tooth, which electrical contact is strongly correlated with thermal contact. Additionally, timing circuitry measures and displays the length of time that the probe tip has been in contact with the tooth so that the precise time at which a patient response occurs may be used to render the diagnosis quantitative. Electrical stimulation is provided by regulating the current that is passed through the probe tip into the tooth rather than the voltage that is applied to the probe tip. This current is applied in pulses, and the amplitude of the current pulses is gradually increased from a minimum value in an automatic fashion so that the patient's sensitivity may be determined. Electrical contact with the tooth is monitored as with the thermal testing.

19 Claims, 16 Drawing Figures

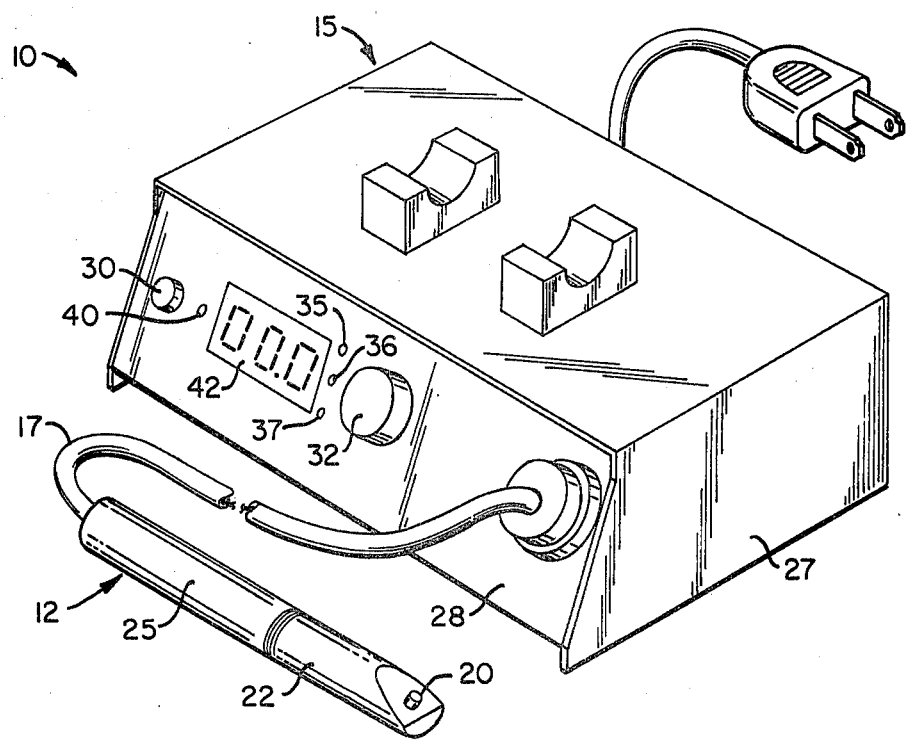
FIG._1.
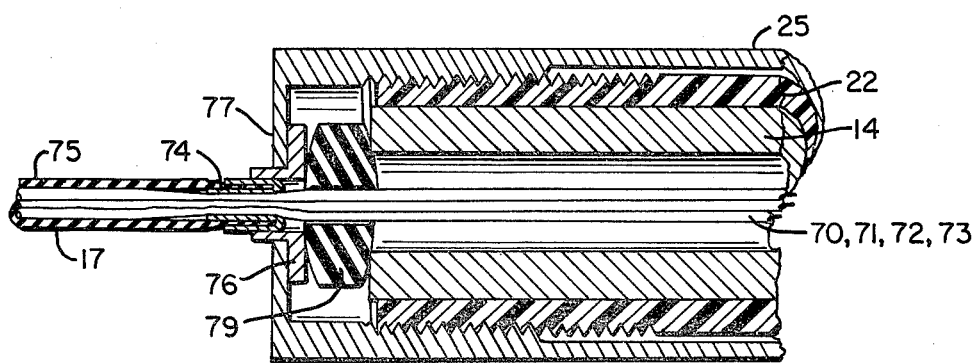
FIG._4.

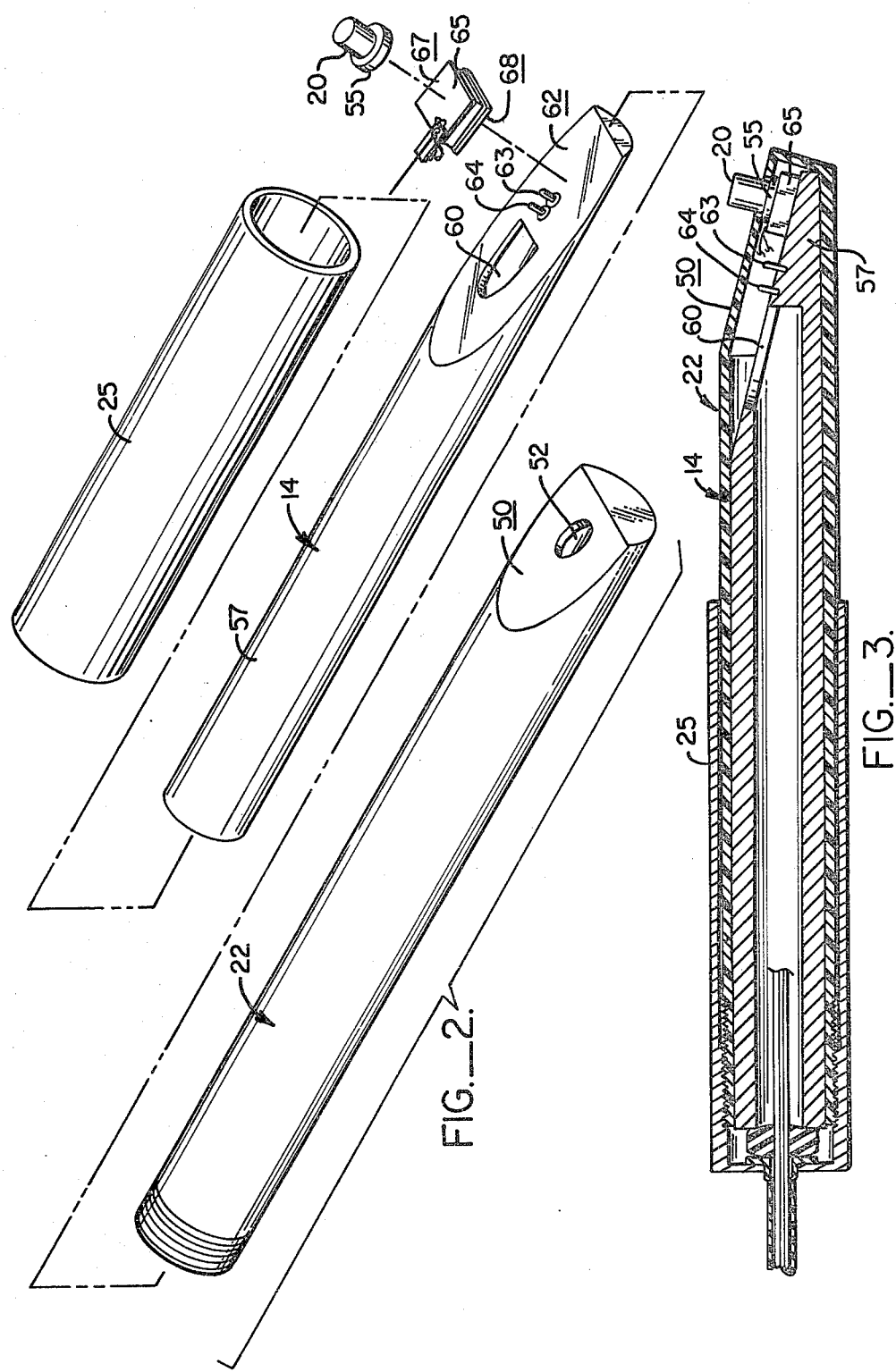

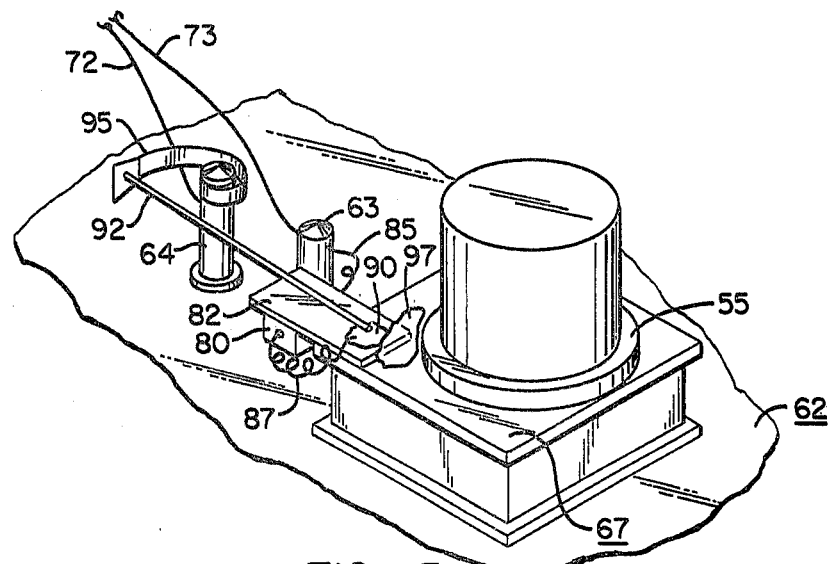
FIG._5.
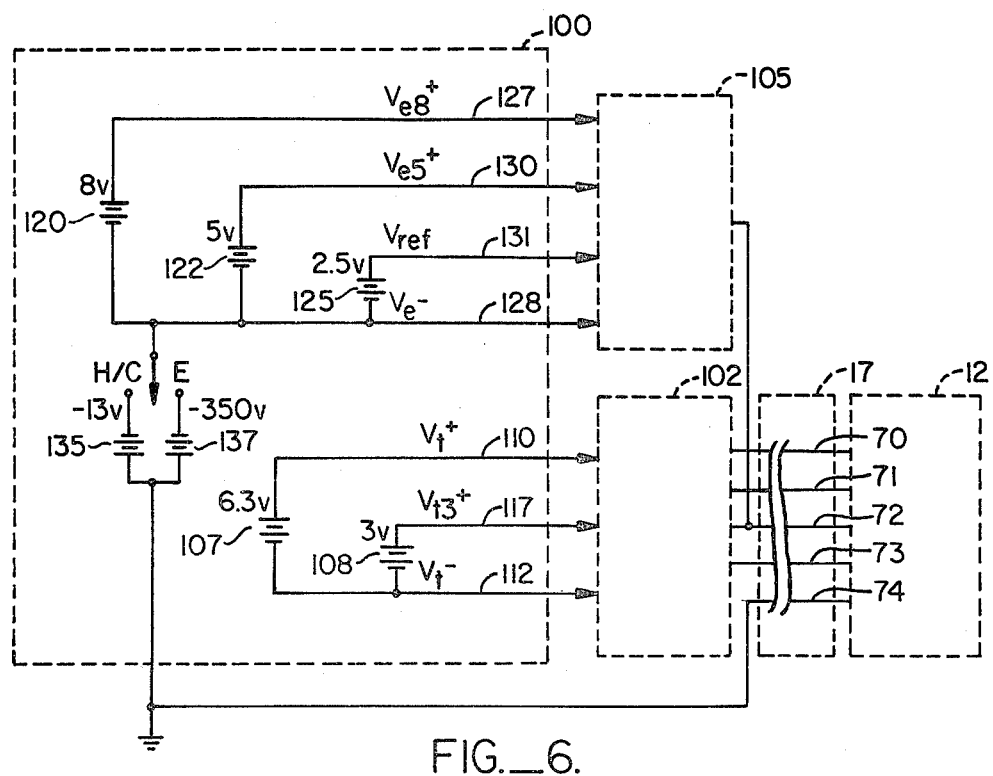
FIG._6.

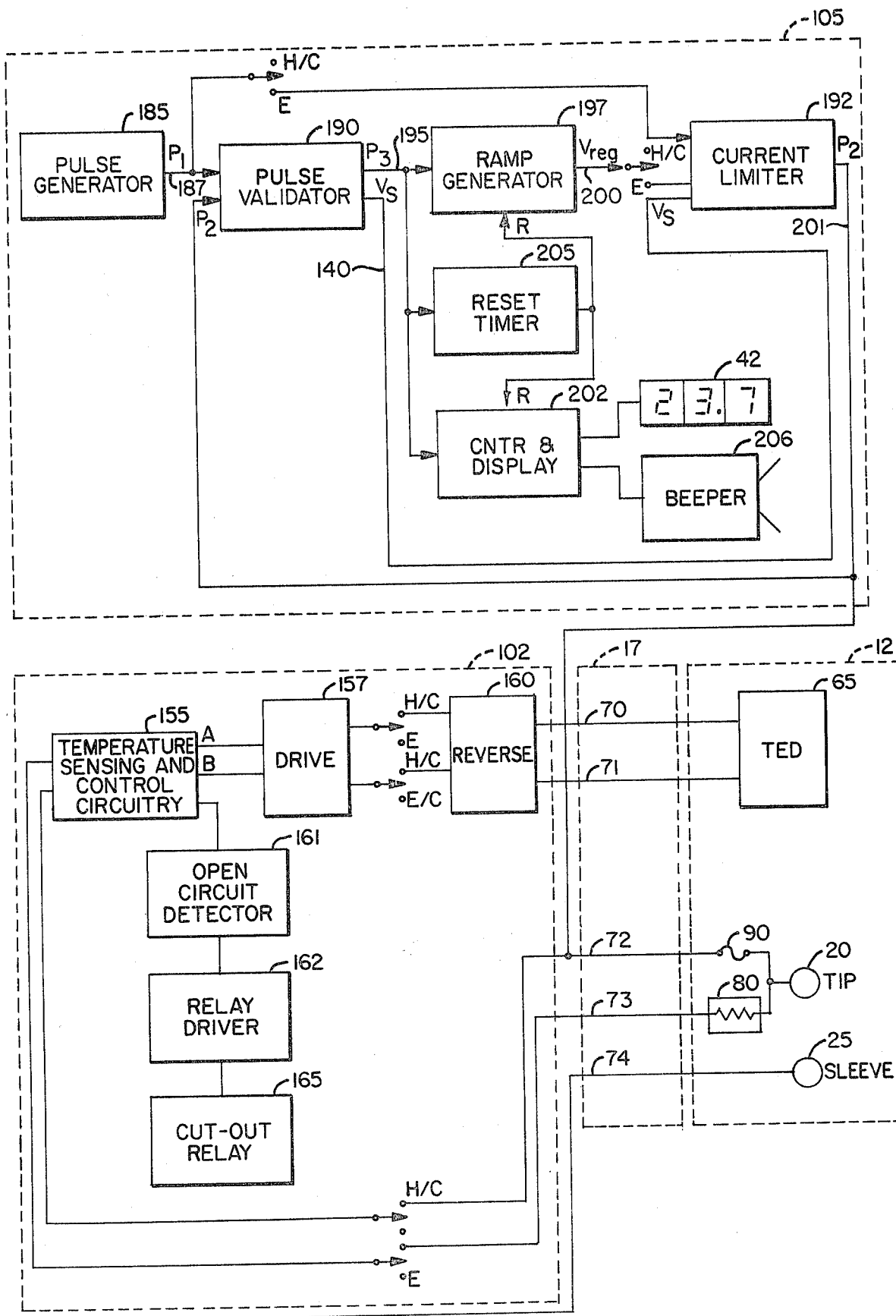
FIG._7.

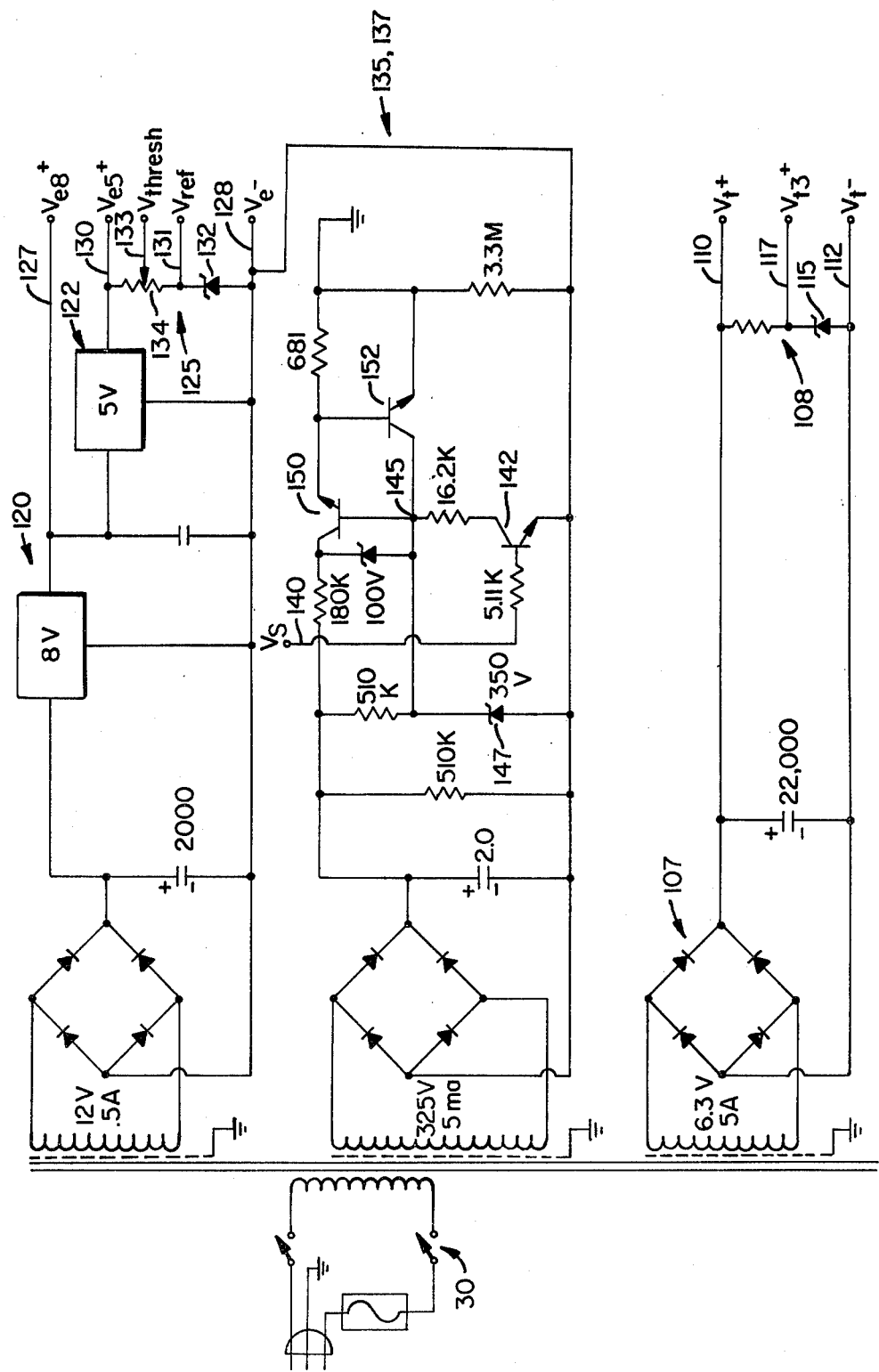
FIG._8.

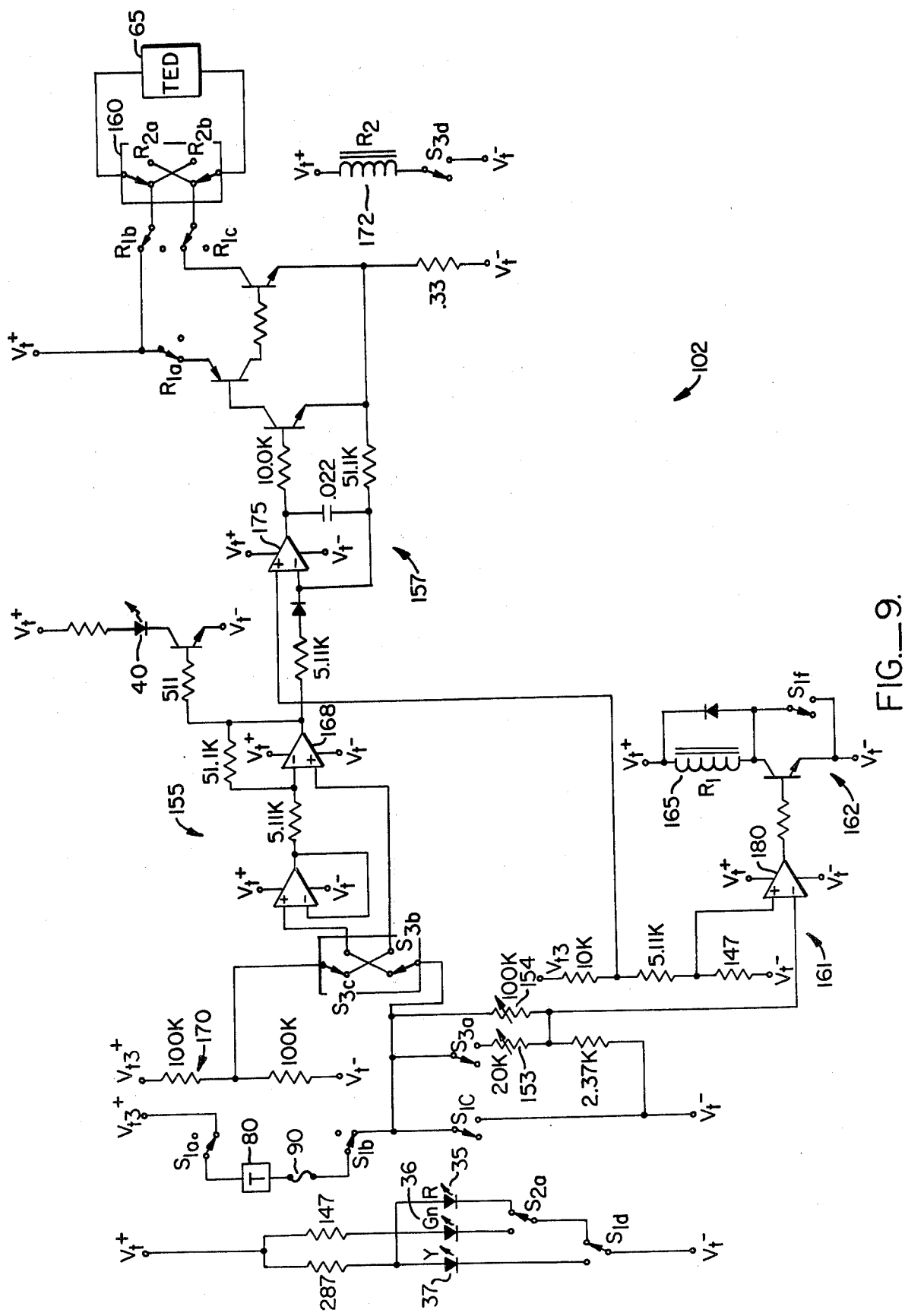
FIG._9.

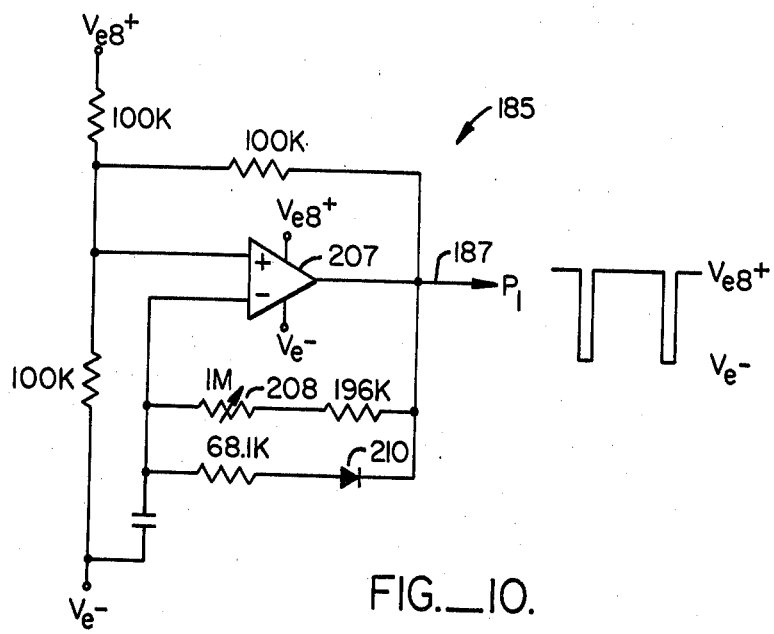
FIG.—10.
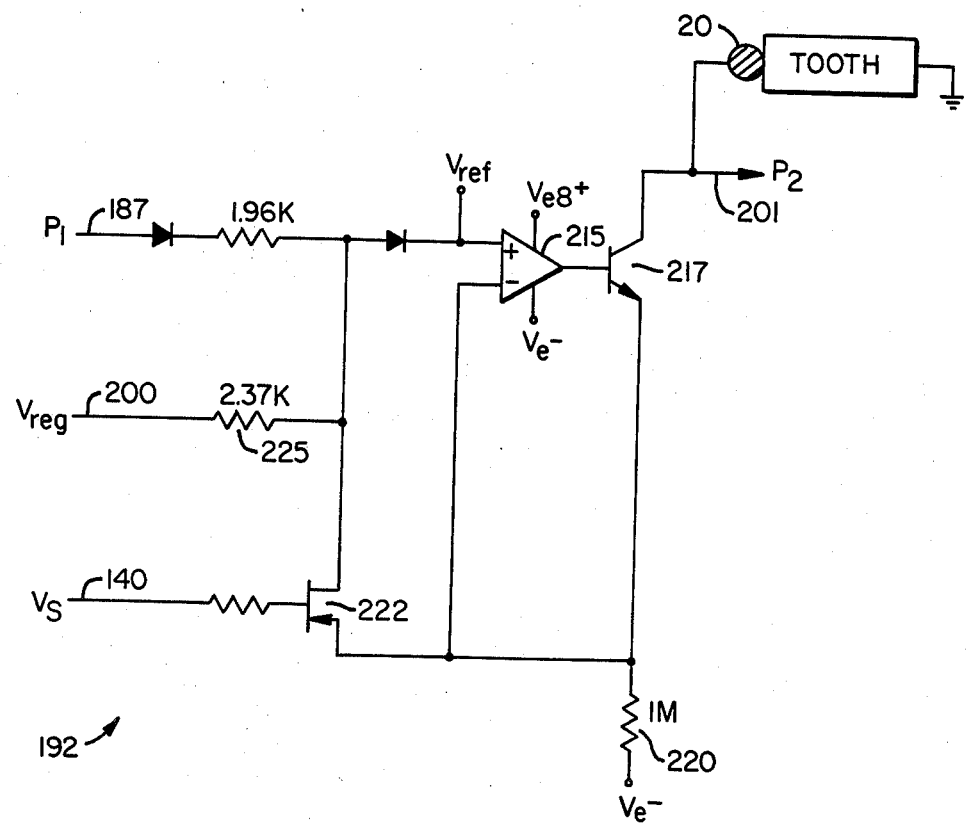
FIG.—11.

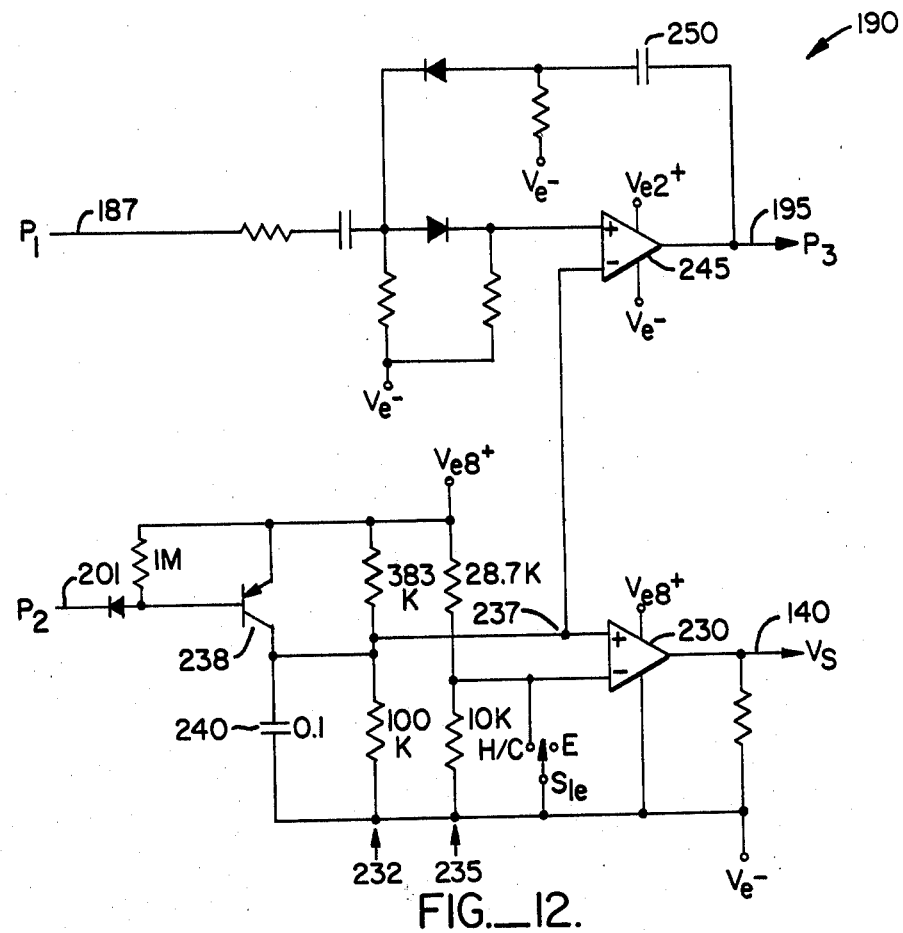
FIG._12.
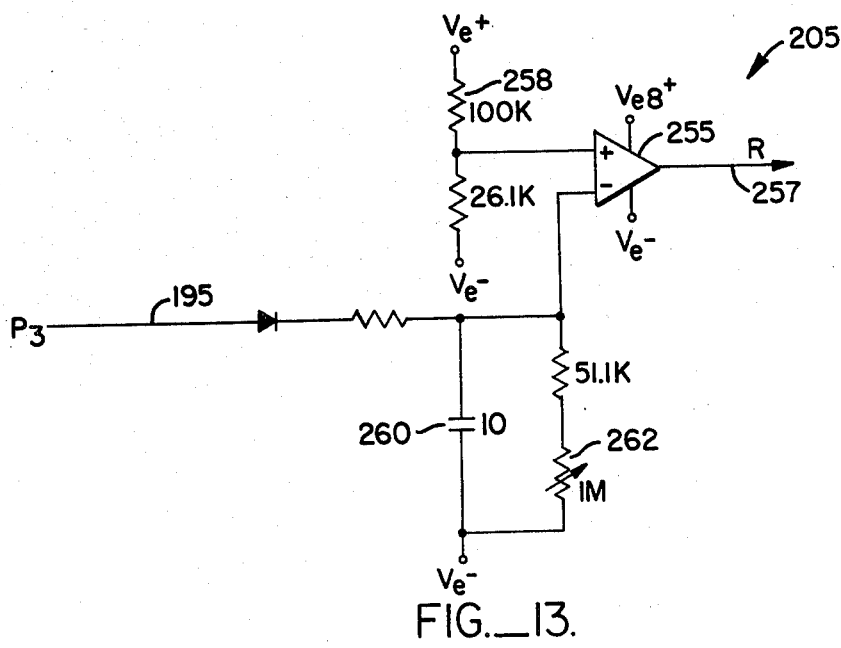
FIG._13.

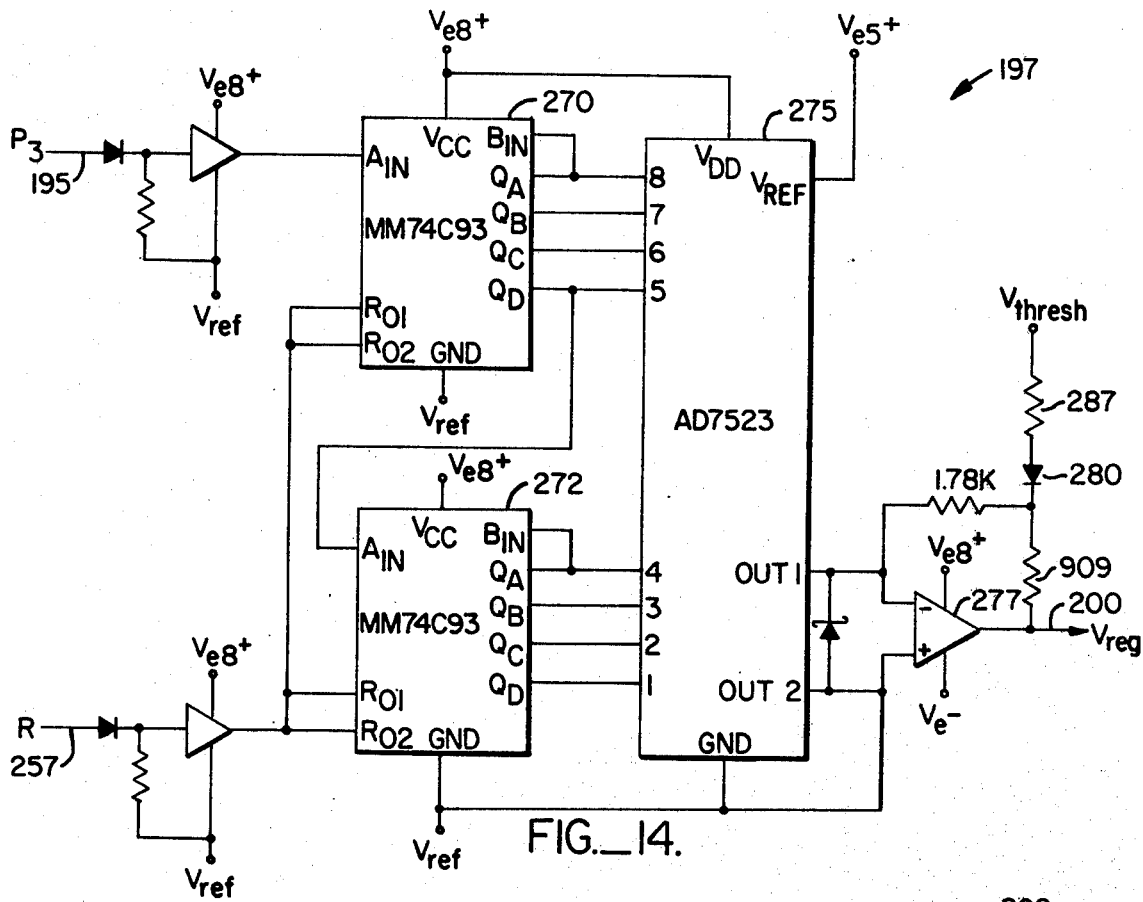
FIG._14.
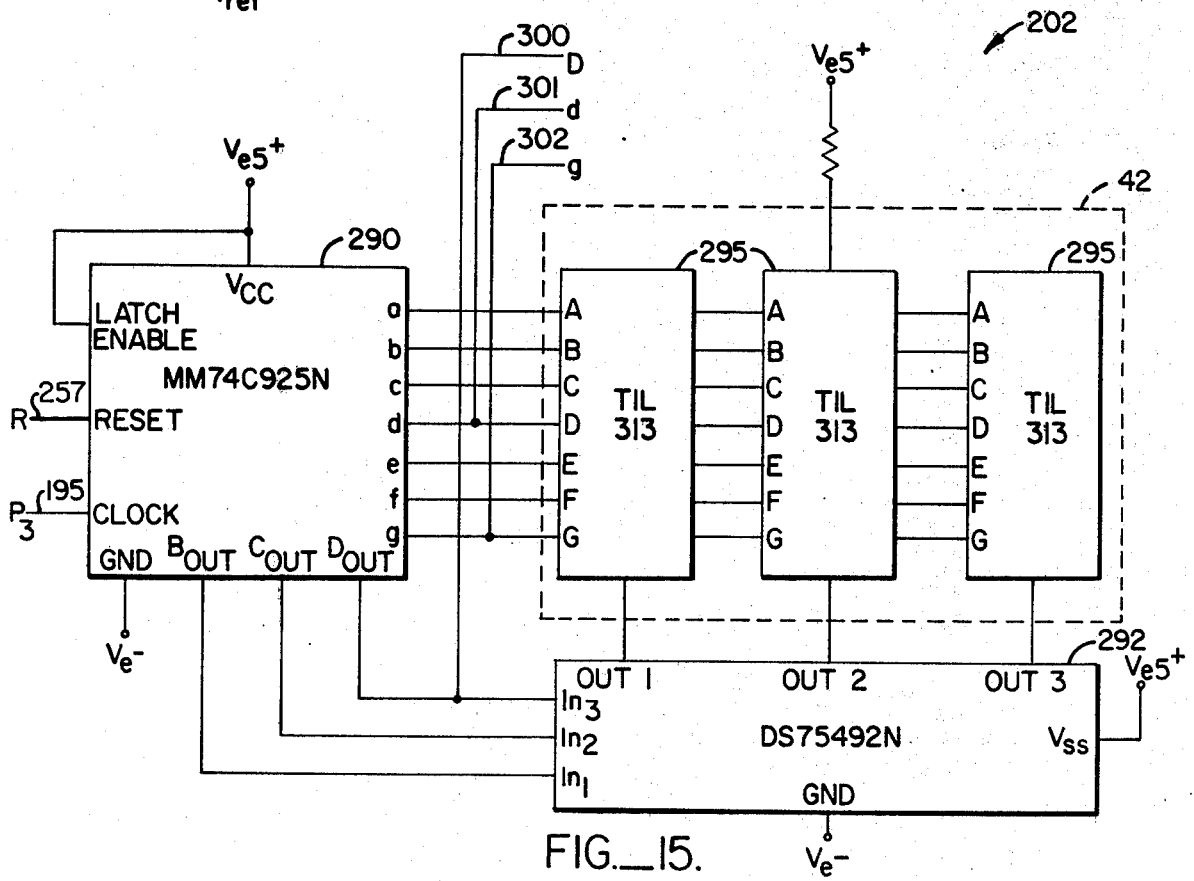
FIG._15.

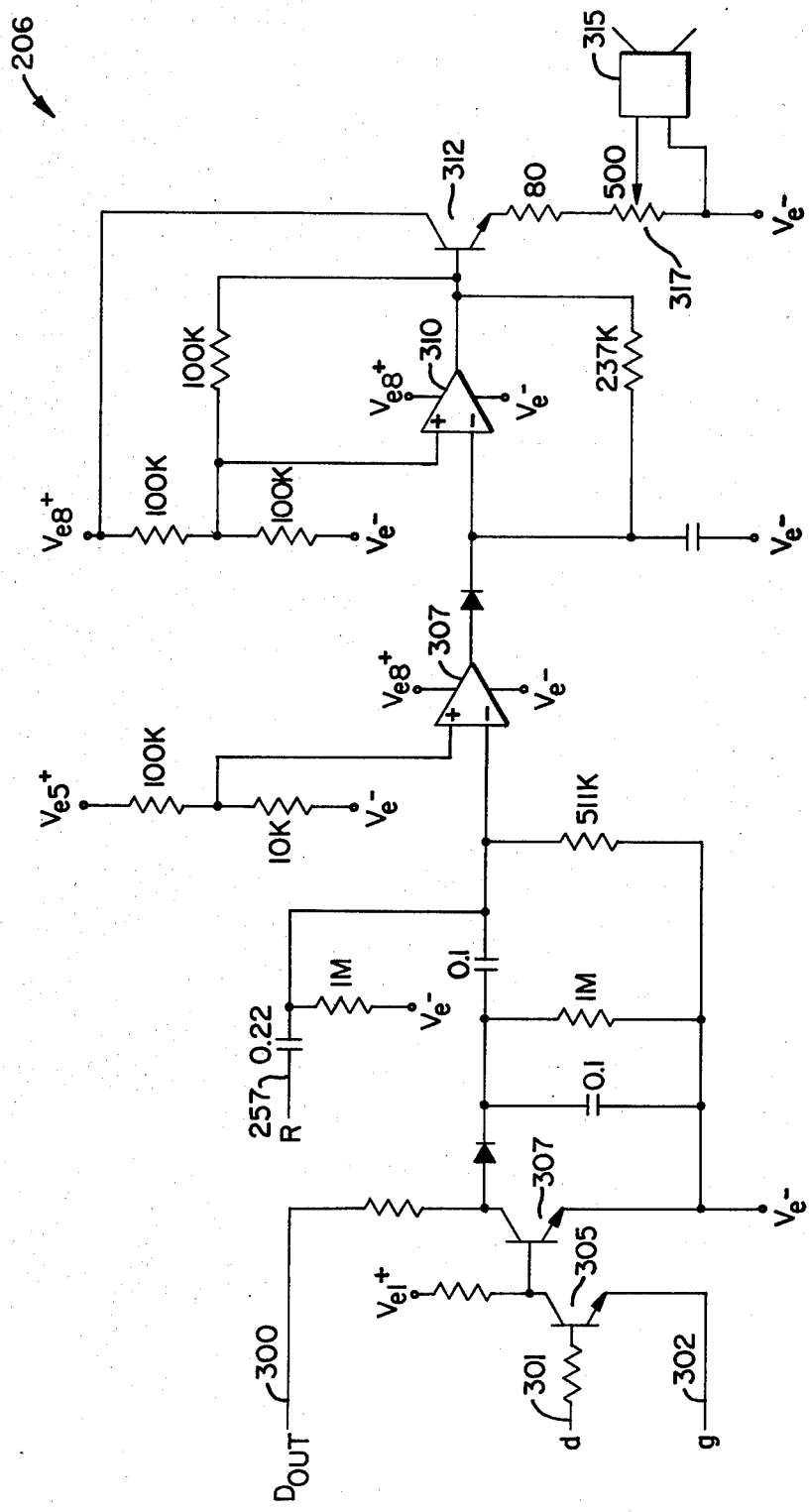
FIG._16.

DENTAL PULP VITALITY TESTER

FIELD OF THE INVENTION

The present invention relates generally to devices for providing local stimulation of selective body portions and more specifically, to a dental pulp vitality tester which provides thermal and electrical stimulation.

BACKGROUND OF THE INVENTION

It is a well known dental technique to evaluate the condition of the tooth pulp by subjecting the tooth to localized stimulation and noting the patient's response. In particular, the tooth may be subjected to electrical stimulation or extremes of heat and cold. Electrical stimulation is typically more convenient, but may be an unsuitable technique under certain circumstances, as for example where a number of teeth are electrically connected by a metallic bridge or similar dental work. Even where electrical testing is available, thermal testing is a useful adjunct, serving as a check on the results of the electrical testing. Moreover, specific known sensitivity to heat and/or cold, as expressed by a patient, can be confirmed by the application of thermal stimulation.

With respect to the localized application of heat or cold, U.S. Pat. No. 3,274,995, to Eidus discloses a dental pulp tester in which a metallic probe tip is thermally coupled to a thermoelectric device utilizing the Peltier effect. The passage of electrical current through the thermoelectric device causes the probe tip to become hot or cold, depending on the polarity of the current. A measure of control over the probe tip temperature is achieved by providing a rheostat to control the current that flows through the thermoelectric device. However, the use of a rheostat control is imprecise. Moreover, even if the rheostat setting may be reproduced, a given amount of current through the thermoelectric device does not necessarily lead to the same temperature of the probe tip, since the temperature may vary depending upon whether the probe tip is in contact with the tooth to be tested or not. Overheating of the probe tip, in addition to possibly subjecting the instrument to damage, represents a source of potential injury to a patient. Nevertheless, the use of a thermoelectric device to provide extremes of temperature represents a substantial improvement over older methods which involved placing ice or volatile liquids directly on the tooth.

With respect to electrical stimulation, it is known to provide a test device having a probe tip to which a controlled high voltage is intermittently applied. Moreover, it is known to provide such an instrument with circuitry for automatically increasing over time the voltage level that is applied to the tip, and circuitry for checking electrical contact between the probe tip and the tooth and resetting the voltage to its lowest level if electrical contact is interrupted for more than a predetermined time.

The use of a controlled voltage for providing localized stimulation is not without its disadvantages. In particular, in the event that a non-vital tooth to be tested is not properly dried, the saliva may provide electrical paths to other vital teeth, thus providing a false indication of vitality. Moreover, if the contact between the probe tip and a vital tooth to be tested is poor, but not sufficiently poor to cause the contact checking circuitry to provide an indication, the voltage actually applied to the tooth is smaller than believed, and a false indication of non-vitality results.

SUMMARY OF THE INVENTION

The present invention provides a dental pulp vitality tester for selectively applying heat, cold, or electrical stimulation to a patient's tooth in a controlled reproducible manner. Broadly, the device comprises a handpiece and a control module which are connected by an electric cable. The handpiece includes a handle having a thermally and electrically conductive probe tip adapted to contact selected body portions (typically teeth), a heat sink within the handle, and a thermoelectric element having a first junction thermally coupled to the probe tip and a second junction thermally coupled to the heat sink. The control unit includes power supply, temperature and current regulation circuitry, and display circuitry.

Heating or cooling of the probe tip is accomplished by passage of electric current through the thermoelectric element, the amount of heating or cooling being dependent upon the direction and magnitude of the current. Reliable, reproducible results are achieved by current regulation. A temperature sensing device such as a thermistor is thermally coupled to the probe tip, and temperature regulation circuitry responsive to the state of the temperature sensing element regulates the current to the thermoelectric element to maintain the temperature of the probe tip constant at a predetermined desired value. Thus, substantially uniform temperature of the probe tip is achieved, thereby increasing the reliability and reproducibility of the test results. It will be readily appreciated that regulating the temperature of the probe tip in this manner minimizes the risk of injury to the patient due to an overheated probe tip. Additionally, a fusible link thermally coupled to the probe tip is electrically interposed within the temperature regulation circuit. In the unlikely event that the probe tip overheats, the fusible link melts, thus resulting in an open circuit which is detected by the temperature regulation circuitry which responds by causing the current to the thermoelectric element to be cut off.

According to a further aspect of the present invention, the probe tip has a flat rear surface, the thermoelectric element has opposed flat faces, and the heat sink has a wedge configuration with a flat face. Movement of the probe tip in a direction away from the thermoelectric element is restrained by suitable means such as a flange on the probe tip, and resilient means is provided for urging the heat sink in a direction that wedges the thermoelectric element between the probe tip and the heat sink to promote intimate thermal contact. This thermal contact is further improved by the use of thermally (and electrically) conductive paste.

According to a further aspect of the present invention, the control module includes circuitry for quantifying the stimulus applied. In particular, circuitry is provided for sensing electrical contact with the tooth, which electrical contact is strongly correlated with thermal contact. Additionally, timing circuitry measures and displays the length of time that the probe tip has been in contact with the tooth so that the precise time at which a patient response occurs may be used to render the diagnosis quantitative. Audible signals are also provided at fixed intervals (e.g., one second) during the time that the probe tip is in contact with the tooth, thus providing a continuous monitor on the contact.

This has the advantage that the dentist can monitor the elapsed time without having to look at the display, so that he can keep his full attention on keeping the probe tip properly positioned.

According to a further aspect of the present invention, electrical stimulation is provided by regulating the current that is passed through the probe tip into the tooth rather than the voltage that is applied to the probe tip. This current is applied in pulses, and the amplitude of the current pulses is gradually increased from a minimum value in an automatic fashion so that the patient's sensitivity may be determined. Electrical contact with the tooth is monitored, and a driving voltage is made available to provide the current pulses of the appropriate desired amplitude. The time interval during which contact has existed is measured and displayed as above. The monitoring has a purpose of checking whether the desired current can be driven with the available voltage. This is checked at the end of the pulse so that the probe capacitance has already been charged up. Otherwise, the current that flows to charge the probe capacitance would indicate electrical contact to the tooth, regardless of whether or not such contact did in fact exist. In the event that electrical contact is found lacking, the high voltage is withheld from the probe tip until contact is reestablished. Thus, the possibility of suddenly applying a high current stimulus to a tooth without the above-mentioned gradual increase is avoided. If electrical contact to the tooth has been broken for more than a predetermined period, the current that may be applied to the tooth upon contact's being reestablished is set to the minimum value and the timer is zeroed. The current is also reset to the minimum value after the maximum current value has been reached.

For a further understanding of the nature and advantages of the present invention, reference should be made to the remaining portions of the specification and the attached drawings.

BRIEF DESCRIPTION OF THE DRAWINGS

FIG. 1 is an isometric view showing the major components of the present invention;

FIG. 2 is an exploded view of the handpiece;

FIG. 3 is a longitudinal sectional view of the handpiece;

FIG. 4 is a detailed sectional view of the butt end of the handpiece;

FIG. 5 is a detailed isometric view of the temperature sensing elements;

FIG. 6 is a block diagram of the power supply circuitry within the control unit;

FIG. 7 is a block diagram of the temperature regulation circuitry and the contact monitoring and current regulation circuitry;

FIG. 8 is a circuit schematic of the power supply circuitry;

FIG. 9 is a circuit schematic of the temperature regulation circuitry;

FIG. 10 is a circuit schematic of the pulse generator;

FIG. 11 is a circuit schematic of the current limiter;

FIG. 12 is a circuit schematic of the pulse validator;

FIG. 13 is a circuit schematic of the reset timer;

FIG. 14 is a circuit schematic of the ramp generator;

FIG. 15 is a circuit schematic of the counter and display circuitry; and

FIG. 16 is a circuit schematic of the beeper circuitry.

DETAILED DESCRIPTION OF THE INVENTION

FIG. 1 is an isometric view illustrating a dental pulp vitality tester 10 according to the present invention. Broadly, the vitality tester includes a handpiece 12, a control unit 15, with suitable electrical connection therebetween supplied by a flexible cable 17. Handpiece 12 includes a metallic probe tip 20, a plastic housing 22 from which probe tip 20 protrudes, and a grounded metallic sleeve 25. In use, probe tip 20 is applied to the tooth to be tested, with the dentist holding handpiece 12 with his hand contacting grounded sleeve 25, and further with either hand contacting the patient's oral mucosa. A dab of toothpaste is normally applied to probe tip 20 to assure good thermal and electrical contact with the tooth. Appropriate circuitry within control unit 15 causes electrical or thermal (either hot or cold) stimulation to be applied to the tooth through probe tip 20. Thermal stimulation is provided by a thermoelectric device to be described below.

The details of the circuitry and operation will be set forth below, but a brief functional description may now be set forth. Control unit 15 includes a housing 27 having a front panel 28 on which are mounted various control switches and indicators. The control switches available to the dentist include an on-off switch 30 and a function selector 32 which may be a 3-position rotary switch for selecting the type of stimulation (hot, cold, electric) to be applied. Depending on the mode of stimulation selected, appropriate test indicator lights are illuminated. These include a "hot" light 35, a "cold" light 36, and an "electric" light 37. A "ready" light 40 is illuminated when the electric test mode is selected or when probe tip 20 is within a few degrees of its desired temperature when either of the hot or cold test modes is selected. A 3-digit display 42 provides a visual indication of the length of time that electrical contact has been established with the tooth being tested so that a patient's response may be correlated with the duration of the appropriate stimulation. As will be discussed below, the electrical stimulation is gradually increased over time so that display 42 provides a quantitative measure of the intensity of stimulation.

Referring to FIGS. 2-4, the construction of handpiece 12 may be seen. In particular, plastic housing 22 is generally tubular in configuration, being truncated obliquely at a first end to define a flat face 50 at a small angle from the cylindrical axis. Face 50 has a circular aperture 52 sized to accommodate probe tip 20. Probe tip 20 has a circular flange 55 at its base to prevent outward movement of probe tip 20 once flange 55 contacts the inner surface of face 50. Mounted within housing 22 is a copper heat sink 57 having a generally cylindrical configuration with a central bore 60 to accommodate electrical leads from cable 17. Heat sink 57 is similarly obliquely truncated to define a flat face 62 that is preferably the same angle to the cylindrical axis as the angle of housing face 50. Insulated terminals 63 and 64 are mounted to and protrude from heat sink face 62.

A thermoelectrical device 65 has parallel metallized faces 67 and 68. Thermoelectric device 65 is sandwiched between heat sink 57 and probe tip flange 55 with surface 67 contacting probe tip flange 55 and surface 68 contacting heat sink face 62. Due to the small angle between face 62 and the cylindrical axis, pressure on heat sink 57 along the cylindrical axis promotes intimate contact of the respective faces of thermoelectric device 65 with heat sink 57 and probe tip 20.

Referring specifically to FIG. 4, a mechanism of providing such mechanical pressure can be seen. Cable 17 is of the type having four electrical conductors 70, 71, 72, and 73 surrounded by a ground shield 74 and outer insulation 75. An outwardly flanged collar 76 is crimped about cable 17, making electrical contact with ground shield 74. Handpiece sleeve 25 has an inwardly facing flange 77 that surrounds cable 17 and collar 76. The flange of collar 76 is located between sleeve flange 77 and heat sink 57. A resilient washer 79 is interposed between the collar flange and heat sink 57 so that as sleeve 25 is threaded onto housing 22, resilient washer 79 is compressed, thus urging heat sink 57 in a direction that wedges thermoelectric device 65 between the heat sink and the probe tip. It should be noted that the flange of collar 76 provides electrical contact between ground shield 74 and sleeve 25, and further provides strain relief for cable 17.

Conductors 70-73 of cable 17 pass through heat sink bore 60, conductors 70 and 71 ultimately being connected to thermoelectric device 65, and conductors 72 and 73 being connected to temperature sensing elements as will now be described. Turning to FIG. 5, a perspective view of the temperature sensing elements may be seen. In particular, a thermistor 80 is epoxied to a mounting plate 82 that is itself epoxied to thermoelectric device surface 67. Thermistor 80 is a two-terminal device, whose resistance varies sharply with temperature. A first terminal of thermistor 80 is connected to a fine wire 85 to insulated terminal 63. The other thermistor terminal is connected by a fine wire 87 to a small pool of low melting point solder 90 (melting point 96° C.) on top of mounting plate 82. Embedded in solder pool 90 is a connecting wire 92 which is maintained under tension by a beryllium copper spring 95 mounted to insulated terminal 64. Thus, under normal conditions, solder pool 90 completes an electrical path from terminal 63 through thermistor 80, to terminal 64.

A conductive patch 97 overlies a portion of solder pool 90 and metallized surface 67 of thermoelectric device 65, thus providing electrical contact between surface 67 (and probe tip 20 in contact therewith) and terminal 64. Thus, solder pool 90 provides a fusible link. In particular, if the top surface of thermoelectric device 65 should heat up beyond 96° C., solder pool 90 melts, allowing spring 95 to pull connecting wire 92 away and open the electrical circuit. As will be discussed later, the result of this is for current to the thermoelectric device to be cut off. Note also that conductive patch 97 provides a direct electrical connection between probe tip 20 and cable conductor 72.

FIGS. 6 and 7 provide an overall block diagram of the circuitry in control unit 15. Broadly, this circuitry comprises power supply circuitry 100, temperature regulation circuitry 102, and contact monitoring and electrical current regulation circuitry 105. Single pole/double throw switches are shown to indicate schematic connections that are open or closed depending on whether the device is in the thermal mode (designated H/C) or the electrical test mode (designated E). As will be discussed more fully below, some of these switches are provided by mechanical contacts (manually or relay controlled), while others are provided by electronic elements.

Turning first to power supply circuitry 100, additional reference should be had to FIG. 8 which provides a full circuit schematic of the power supply circuitry. Broadly, power supply circuitry 100 provides power for temperature regulation circuitry 102 and contact monitoring and current regulation circuitry 105. The supplies for temperature regulation circuitry 102 include a 6.3-volt supply 107 and a 3-volt supply 108. Supply 107 provides filtered full-wave rectified power on a line 110, designated $V_t+$ with respect to a line 112, designated $V_t-$. Supply 108 is derived therefrom using a Zener diode 115, and supplies 3 volts on a line 117, designated $V_{t3}+$.

The supplies for contact monitoring and current regulation circuitry 105 include an 8-volt power supply 120, a 5-volt supply 122, and a 2.5-volt supply 125. Supply 120 provides a regulated 8 volt level on a line 127, designated $V_{e8}+$ with respect to a common line 128, designated $V_e-$. Supply 122 provides a regulated 5-volt level on a line 130, designated $V_{e5}+$, while supply 125 supplies a 2.5 volt level on a line 131, designated $V_{ref}$. Power supplies 120 and 122 incorporate appropriate regulators while supply 125 is derived from supply 122 using a Zener diode 132. A variable voltage, between $V_{ref}$ and $V_{e5}+$ is tapped off a potentiometer 134 and withdrawn on a line 133, designated $V_{thresh}$.

Depending on whether the device is in the thermal or electrical test mode, $V_e-$ line 128 is selectively coupled to either of a $-13$ volt power supply 135 or a $-350$ volt power supply 137 as measured with respect to ground. The control is established by the voltage level, designated $V_s$, on a line 140, when $V_s$ is low, relative to $V_e-$, a control transistor 142 is cut off, thus holding a control current point 145 at approximately 350 volts above $V_e-$, as defined by a Zener diode 147. When $V_s$ is at 8 volts, relative to $V_e-$, transistor 142 conducts, and circuit point 145 drops to 13 volts above $V_e-$. Circuit point 145 is coupled to the base of a transistor 150 and the collector of a transistor 152, the base of the latter being coupled to the emitter of the former. When circuit point 145 is at the 350 volt level, transistor 150 conducts and has its current limited by transistor 152 which robs base current to limit the current through transistor 150 to approximately 1 milliamp. The emitter of transistor 152 is grounded and the emitter of transistor 142 is coupled to $V_e-$ line 128. Therefore, $V_e-$ line 128 is held at the negative of the voltage level at circuit point 145, relative to ground.

Turning next to temperature regulation circuitry 102, additional reference should be had to the circuit schematic shown in FIG. 9. A number of switch contacts are shown, being designated by the prefixes $S_1$, $S_2$, and $S_3$. These are contacts activated by function control selector 32, with the $S_1$ contacts controlling whether the device operates in the thermal or electrical mode, and the $S_3$ contacts determining whether in the hot or the cold mode. Broadly, the temperature regulation circuitry provides a constant DC current of 3 amps to thermoelectric device 65 until probe tip 20 reaches the correct temperature as determined by the resistance of thermistor 80. In this context, the correct temperature is approximately $-5°$ C. in the cold mode and approximately 70° C. in the hot mode, and is adjustable by appropriate potentiometers 153 and 154 for hot and cold, respectively.

Appropriate temperature sensing and control circuitry 155 incorporates thermistor 80 as part of a voltage divider and compares the voltage with appropriate reference level voltages as defined by predetermined voltage dividers. Temperature sensing and control circuitry 155 supplies signals to appropriate driving circuitry 157. As the temperature approaches the correct value, the current supplied by current driver 157 is reduced. A reversing switch 160 is provided to reverse the polarity of current through thermoelectric device 65, depending upon whether heating or cooling of probe tip 20 is required. Sensing and control circuitry 155 also supplies signals to an open circuit detector 161 which is coupled to a relay driver 162. In the event that an open circuit, indicative of the melting of solder pool 90, is detected, relay driver 162 is activated to energize a cut-out relay 165 to cut off current to thermoelectric device 65. Cut-out relay 165 is also activated when the instrument is operated in the electrical test mode.

Referring specifically to FIG. 9, temperature sensing and control circuitry 155 incorporates thermistor 80 and potentiometers 153 and 154 into a voltage divider. A comparator 168 compares this voltage level with a standard level defined by a voltage divider 170. The output of comparator 168 is used to drive "ready" light 40, and is compared to a further standard voltage level by a comparator 175 which supplies signals to driving circuitry 157. Open circuit detection circuitry 161 includes a comparator 180 which activates cut-out relay 165 in the event that solder pool 90 melts. Cut-out relay 165 is also activated when the device is operated in the electrical test mode. Thermoelectric reversing switch 160 is activated by a relay 172, itself controlled by a single set of contacts on switch $S_3$.

Turning next to contact monitoring and current regulation circuitry 105, the general operation will now be described with reference to the block diagram shown in FIG. 7. Two main functions are performed. First, in all modes, the electrical contact between probe tip 20 and the tooth being tested is monitored by passing a constant current of 2.5 microamps to probe tip 20. A counter is incremented to reflect the time that such electrical contact has existed and the result displayed. Second, in the electrical test mode, so long as electrical contact is maintained, negative current pulses beyond the 2.5 microamps are fed to the probe tip and the amplitude of these pulses is gradually increased so that the patient's sensitivity may be correlated with the magnitude of the stimulus. These current pulses have a magnitude that ranges up to about 450 microamps, the driving voltage being supplied by −350 volt power supply 137.

More specifically, a pulse generator 185 supplies pulses on a line 187, designated $P_1$, to a pulse validator 190, and, in the electrical test mode, to a current limiter 192 as well. Pulse validator 190 produces corresponding pulses on a line 195, designated $P_3$, so long as electrical contact has existed for more than about 1/10 second. The pulses are fed to a ramp generator 197 which generates a voltage on a line 200, designated $V_{reg}$, that controls current limiter 192. Current limiter 192 supplies controlled current pulses through probe tip 20 on a line 201, designated $P_2$, the voltage on which is monitored by pulse validator 190. Additionally, pulse validator 190 provides voltage $V_s$ on line 140 with $V_s$ being high (making only −13 volts available to the probe tip) when the device is in the thermal test mode or when insufficient contact exists. Pulses on $P_3$ line 195 are also fed to counter and display circuitry 202 and to a reset timer 205. Counter and display circuitry displays the count in numeric form on display 42 and drives beeper circuitry 206 to provide periodic audible signals when contact is being made with the tooth. If more than a few seconds elapse with pulses not being supplied to reset timer 205, the output from ramp generator 197 is reset so that minimum current is allowed by current limiter 192, and the display is zeroed.

In connection with the following description of the individual control blocks within contact monitoring and current regulation circuitry 105, additional reference should be made at appropriate times to FIGS. 10–16.

Turning first to pulse generator 185, additional reference should be made to the circuit schematic of FIG. 10. As can be seen, an operational amplifier 207 forms the active component of an oscillator having a variable frequency, preferably in the range of 5 to 20 Hertz, as determined by the setting of a potentiometer 208 in the feedback circuit. A diode 210 provides asymmetry with the results that $P_1$ line 187 is for the most part high (at level $V_{e8}+$) with low going pulses (to level $V_e-$) of approximately 0.01 second duration at the oscillator frequency. As discussed above, these pulses are communicated to pulse validator 190 and, in the electrical test mode, to current limiter 192 as well.

Turning next to current limiter 192, additional reference should be made to the circuit schematic of FIG. 11. An operational amplifier 215 controls the base of a pass transistor 217 to provide a current path through a 1 megaohm resistor 220. The positive input of amplifier 215 is held at $V_{ref}$ which is 2.5 volts, thus limiting the current through resistor 220 (coupled to the negative input) to 2.5 microamps. This 2.5 microamp current flows constantly. However, if $V_s$ is low, as is the case when electrical contact is satisfactory in the electrical test mode, and $P_1$ is low, a gating transistor (FET) 222 is turned on to provide an additional current path through a 2.37 K resistor 225. The levels on $P_1$ line 187 and $V_{reg}$ line 200 are communicated through appropriate resistors and diodes to an input of operational amplifier 215. As will be discussed below, $V_{reg}$ starts out at 2.5 volts and is lowered to approximately 1.5 volts. Thus, as $V_{reg}$ is lowered, additional current is allowed to flow through pass transistor 217. It should be noted that under a condition of poor electrical contact between probe tip 20 and the tooth to be tested, the voltage on $P_2$ line 201 drops below that on $V_{e8}+$ line 127, which fact is used by pulse validator 190 to keep $V_s$ high as will be described below.

Turning next to pulse validator 190, additional reference should be made to the circuit schematic of FIG. 12. A first operational amplifier 230 controls $V_s$ line 140. Voltage dividers 232 and 235 hold a circuit point 237 coupled to the positive input of operational amplifier 230 below the level of the negative input so that $V_s$ line 140 is low. In the thermal test mode, the negative input of amplifier 230 is shorted to ground so that $V_s$ goes high. Additionally, circuit point 237 is coupled to a transistor 238 controlled by $P_2$ line 201 so that when $P_2$ line 201 is more than approximately a volt below $V_{e8}+$ line 127, transistor 238 turns on and pulls circuit point 237 (and the positive input of amplifier 230) high, thus making $V_s$ high. A capacitor 240 coupling control points 237 to ground keeps control point 237 above the value defined by resistive divider 232 for a predetermined time (say approximately 1/10 second) even after $P_2$ goes high again.

A second operational amplifier 245 controls $P_3$ line 195. Control point 237 is coupled to the negative input of amplifier 245 so that $P_3$ remains low whenever control point 237 is high. Thus, $P_3$ remains low if $P_2$ has fallen more than approximately a volt below $V_{e8}+$ at any time during the past 1/10 second or so. If $P_2$ has remained no lower than about $V_{e8}+$, control point 237 is relatively low, so that amplifier 245 can respond to signals at its positive input. Pulses on $P_1$ line 187 are capacitively coupled to the positive input which is resistively coupled to $V_e-$. Thus, the positive input of amplifier 245 is normally low and $P_3$ is low. However, in view of the fact that $P_1$ is normally high with pulses being a low transition followed by a high transition, the rising edge on $P_1$ line 187 results in a positive spike at the positive input of amplifier 245, thus producing a positive pulse on $P_3$ line 195. A capacitor 250 at the output of amplifier 245 keeps $P_3$ high long enough to reliably pulse counter and display circuitry 202 and to charge reset timer 205, as will be described below. Thus, it can be seen that pulse validator 190 generates a positive pulse corresponding to each pulse on $P_1$ line 187 for which the level on $P_2$ line 201 has not been more than about a volt below $V_{e8}+$ for the 1/10 second preceding the end of the $P_1$ pulse. The reason for generating the $P_3$ pulse based on the level on $P_2$ line at times including the end of the $P_1$ pulse is to ensure that the level on line $P_2$ accurately reflects the state of the electrical contact between probe tip 20 and the tooth being tested. In particular, early in the $P_1$ pulse, current flows to charge the probe capacitance, and testing the sufficiency of contact before the probe capacitance is fully charged would provide an erroneous indication of electrical contact since current would be flowing.

Turning next to reset timer 205, reference should be made to the circuit schematic of FIG. 13. An operational amplifier 255 maintains a low level on its output which is coupled to a line 257, designated R, so long as positive pulses appear on $P_3$ line 195 at the expected intervals. To this end, the positive input is biased at a fixed voltage by a voltage divider 258 while the $P_3$ pulses are communicated to an RC network 260 coupled to the negative input of amplifier 255. A positive pulse on $P_3$ line 195 charges capacitor 260 which then discharges slowly enough to keep the negative input above the positive input for a predetermined interval. If $P_3$ pulses stop coming, capacitor 260 ultimately discharges so that the negative input falls below the positive input, thus producing a high level on R line 257. The time constant which is adjustable by a potentiometer 262 permits an interval of up to several seconds to elapse before resetting to allow the dentist to read display 42 before it is reset to 0.

Turning next to ramp generator 197, reference should be made to the circuit schematic of FIG. 14. Binary counters 270 and 272 are cascaded to provide an 8-bit count of $P_3$ pulses arriving at the input of counter 270. R line 257 is coupled to the reset inputs on the counters, so that when $P_3$ pulses have been absent for the predetermined time interval, counters 270 and 272 are reset to zero. The binary outputs from counters 270 and 272 are communicated to a multiplying digital to analog converter 275, the analog output of which is amplified by an operational amplifier 277 and then communicated to $V_{reg}$ line 200. In particular, $V_{reg}$ line 200 is 2.5 volts for a binary count of zero, and decreases as the count increases, ultimately reaching a level of about 1.5 volts. A diode 280 within the resistive feedback network couples $V_{reg}$ line 200 to $V_{thresh}$, so that once $V_{reg}$ falls to a predetermined level, diode 280 becomes conductive so that the subsequent falloff of $V_{reg}$ with increasing count becomes relatively more rapid. As stated below, as $V_{reg}$ becomes lower, current limiter 190 permits a greater current to flow to the probe tip. In particular, the current increment is about 1.5 microamps per pulse for the first 200 pulses, and then 3 microamps per pulse until the 256th pulse which resets the counters.

Turning next to counter and display circuitry 202, reference should be made to the circuit schematic of FIG. 15. A counter/driver 290, in particular a 4-digit counter with multiplexed 7-segment output driver, receives pulses on $P_3$ line 195 at its clock input and has its reset input coupled to R line 257. The digit select lines are communicated to a display driver 292 while the segment select lines communicate to 7-segment displays 295 in order to display the pulse count in the format XX.X where the least significant digit increments once for each pulse on $V_3$ line 195. When potentiometer 208 in pulse generator 185 is adjusted to provide a pulse frequency of 10 Hertz, the reading on display 42 provides an indication of valid stimulus time in seconds. Regardless of the pulse frequency, in the electrical test mode, the number displayed gives an unambiguous indication of the pulse stimulus current as determined by the value of $V_{reg}$ output from ramp generator 197. Control lines 300, 301, and 302, designated D, d, and g, are coupled to the least significant digit select output, the lower horizontal segment output, and the middle horizontal segment output, respectively, of counter/driver 290. These lines are used to control beeper circuitry 206. In particular, d line 301 is high, g line 302 is low, and D line 300 is high when and only when the least significant digit is a 0. If the pulse generator frequency is 10 Hertz, this condition occurs once a second.

Turning next to beeper circuitry 206, reference should be made to the circuit schematic of FIG. 16. Cascaded transistors 305 and 307 produce a positive pulse at the negative input of an operational amplifier 307 when lines 300–302 indicate a zero in the least significant digit. The positive input of amplifier 307 is biased at a fixed voltage and the output is coupled to a second operational amplifier 310. Operational amplifier 310 is connected in an audio oscillator configuration, the oscillator being turned on when the negative input of amplifier 310 goes low, which occurs every tenth $P_3$ pulse as described above. The oscillator drives a speaker control transistor 312 which activates a speaker 315. R line 257 is capacitively coupled to the negative input of amplifier 307, thus producing a relatively longer audible beep when R goes high. Hence, the dentist is provided with a way of estimating the stimulus time (for thermal testing) or the intensity (for electrical testing) without having to look at display 42. If the beeps stop occurring, the dentist knows that the probe tip is not making sufficient contact with the tooth. The extra long beep makes known that the counter and ramp generator have been reset. The loudness of the beep is adjustable by a potentiometer 317.

In summary, it can be seen that the present invention provides a most versatile diagnostic instrument that permits precise and quantitative testing to be done in a reproducible and reliable manner. While the above provides a full and complete disclosure of the preferred embodiment of the invention, various modifications, alternate constructions, and equivalents may be employed without departing from the true spirit and scope of the invention. For example, the particular logic circuitry shown for producing particular results under particular conditions made extensive use of operational amplifiers since these elements are inexpensive and reliable. In many instances, digital logic elements such as AND gates, OR gates, and the like could be employed as well. Therefore, the above description and illustrations should not be construed as limiting the scope of the invention which is defined by the appended claims.

We claim:

1. A device for providing local stimulation of a selected portion of a subject's body by subjecting said body portion to heat transfer, comprising:
   a heat conductive probe tip;
   a heat sink;
   a thermoelectric element having a first junction thermally coupled to said tip, a second junction thermally coupled to said heat sink, and electric current path means, said thermoelectric element having the property that the passage of electric current through said electric current path means causes heat transfer between said first and second junctions to occur, the direction of said heat transfer depending on the direction of said electric current;
   current providing means for making available an electric current to said thermoelectric element, said current providing means being operatively coupled to said electric current path means;
   temperature selection means defining a desired one of at least two predetermined temperatures;
   temperature sensing means thermally coupled to said probe tip; and
   current regulation means operatively coupled to said current providing means and responsive to said temperature sensing means and to said temperature selection means for automatically varying the electric current provided by said current providing means to maintain said probe tip at said desired temperature.

2. The invention of claim 1 wherein said temperature sensing means is a thermistor and wherein said current regulation means includes means for incorporating said thermistor into a voltage divider for comparison with a standard voltage.

3. The invention of claim 1, and further comprising a fusible link thermally coupled to said probe tip and forming an electrical connection in said current regulation means such that said fusible link melts upon excessive heat being transferred by said thermoelectric element to said probe tip, said current regulation means including means responsive to said melting of said fusible link and operative to cause said electric current to said thermoelectric element to be interrupted upon said melting.

4. A device for providing local stimulation of a selected portion of a subject's body by subjecting said body portion to heat transfer, comprising:
   a heat conductive probe tip;
   a heat sink;
   a thermoelectric element having a first junction thermally coupled to said tip, a second junction thermally coupled to said heat sink, and electric current path means, said thermoelectric element having the property that the passage of electric current through said electric current path means causes heat transfer between said first and second junctions to occur, the direction of said heat transfer depending on the direction of said electric current;
   current providing means for making available an electric current to said thermoelectric element, said current providing means being operatively coupled to said electric current path means;
   means responsive to the electrical resistance between said probe tip and said body portion; and
   means for measuring and displaying an indication representative of the time interval during which said probe tip is in substantial contact with said body portion.

5. The invention of claim 4 wherein said means responsive to the electricl resistance between said probe tip and said body portion comprises:
   means for passing a constant feeble current through said body portion and probe tip including means for applying a low voltage to said probe tip; and
   means electrically coupled to said probe tip and responsive to a condition wherein the voltage drop across said contact between said probe tip and said body portion is too high to allow said constant feeble current to flow.

6. The invention of claim 4, and further comprising:
   means for zeroing said time interval if a condition of high electrical resistance between said probe tip and said body portion remains for more than a predetermined interval.

7. A device for providing local stimulation of a selected portion of a subject's body by subjecting said body portion to heat transfer, comprising:
   a heat conductive probe tip;
   a heat sink;
   a thermoelectric element having a first junction thermally coupled to said tip, a second junction thermally coupled to said heat sink, and electric current path means, said thermoelectric element having the property that the passage of electric current through said electric current path means causes heat transfer between said first and second junctions to occur, the direction of said heat transfer depending on the direction of said electric current;
   current providing means for making available an electric current to said thermoelectric element, said current providing means being operatively coupled to said electric current path means;
   means constraining motion of said probe tip away from said thermoelectric element;
   said heat sink having a wedge portion contacting said thermoelectric element; and
   means resiliently urging said heat sink wedge portion against said thermoelectric element to wedge said thermoelectric element between said probe tip and said heat sink and thus promote thermal contact between said probe tip and said first junction, and between said heat sink and said second junction.

8. A device for providing localized electrical stimulation of a selected portion of a subject's body comprising:
   an electrically conductive probe tip;
   means for supplying a driving voltage at periodic intervals for driving a current pulse of predetermined amplitude through said probe tip and body portion;
   current regulation means for gradually increasing the predetermined current amplitude on successive pulses;
   means responsive to the electrical resistance between said probe tip and said body portion;
   means for suspending said gradual increase in predetermined amplitude under a condition wherein the electrical resistance between said probe tip and said body portion is too high to allow said driving voltage to drive a current pulse of said predetermined amplitude; and means for withholding said driving voltage under said condition of high resistance.

9. The invention of claim 8 wherein said means for supplying a driving voltage and said current regulation means together comprise:
  pulsing means for providing a cyclical pulse train;
  means responsive to said cyclical pulse train for producing a regulating voltage that varies gradually over a range, said variation occurring only if said pulses of said cyclical pulse train are received;
  means for providing a current path in series with said selected body portion, a point in said current path being coupled to said regulating voltage so that the current that may flow through said path is controlled by the magnitude of said regulating voltage;
  switch means interposed within said current path for selectively blocking and passing current; and
  means for causing said switch means to pass current in synchronization with said cyclical pulse train so that said current flows through said current path in synchronization with said pulse train, said current pulses being characterized by a gradual increase in amplitude as said regulating voltage varies over said range.

10. The invention of claim 9 wherein said suspending and withholding means together comprise:
  means for sensing the voltage drop across the junction between said probe tip and said selected body portion;
  means for withholding said pulses of said cyclical pulse train from said means for producing said regulating voltage upon the detection of a high resistance contact with said probe tip such that said regulating voltage does not change during a period of poor electrical contact; and
  means for keeping said switch means open upon said detection of a high voltage drop across the junction between said probe tip and said body portion so that no current may flow in said current path.

11. The invention of claim 10, and further comprising:
  a reset timer for setting said regulating voltage to the level corresponding to minimum current after a predetermined period of poor electrical contact between said probe tip and said selected body portion.

12. The invention of claim 8, and further comprising:
  means for measuring the time that a condition of low resistance between said probe tip and said body portion has been maintained.

13. A device for testing physiological response of a selected portion of a subject's body by providing local electrical or thermal stimulation, comprising:
  a thermally and electrically conductive probe tip;
  a heat sink;
  a thermoelectric unit having a first junction in thermal contact with said probe tip, a second junction in thermal contact with said heat sink, and current path means, the passage of current through which causes heat transfer between said first and second junctions, the direction and magnitude of said heat transfer being correlated with the direction and magnitude of said current through said current path means;
  current supply means for passing current through said current path means;
  current regulation means for maintaining said probe tip at a predetermined desired temperature;
  current pulse supply means for supplying repeated electric current pulses to said probe tip by making available a driving voltage sufficiently high to cause current pulses of a predetermined desired amplitude to flow;
  means for varying said predetermined desired current over a range; and
  selection means for selectively enabling either of said current supply means and said current pulse supply means.

14. The invention of claim 13, and further comprising:
  means responsive to the electrical resistance between said probe tip and said body portion; and
  means for measuring and displaying an indication representative of the time interval during which said probe tip is in substantial contact with said body portion.

15. The invention of claim 14, and further comprising:
  means for zeroing said time interval if a condition of high electrical resistance between said probe tip and said body portion remains for more than a predetermined interval.

16. The invention of claim 13, and further comprising:
  means responsive to the electrical resistance between said probe tip and said body portion;
  means for suspending said gradual variation in predetermined amplitude under a condition wherein the electrical resistance between said probe tip and said body portion is too high to allow said driving voltage to drive a current pulse of said predetermined amplitude;
  means for withholding said driving voltage under said condition of high resistance; and
  means for measuring the time that a condition of low resistance between said probe tip and said body portion has been maintained.

17. The invention of claim 1, and further comprising means responsive to said temperature sensing means and to said temperature selection means for providing an indication that the temperature of said probe tip is within a small temperature deviation from said desired temperature.

18. The invention of claim 1, and further comprising means responsive to the electrical resistance between said probe tip and said body portions; and
  means for measuring and displaying an indication representative of interval during which such probe tip is in substantial contact with said body portion.

19. The invention of claim 18 or 4 or 14 wherein said means for measuring and displaying includes means for providing an audible indication.

* * * * *

UNITED STATES PATENT AND TRADEMARK OFFICE
CERTIFICATE OF CORRECTION

PATENT NO. : 4,308,012
DATED : Dec. 29, 1981
INVENTOR(S) : Richard Tamler and Edward B. Stoneham It is certified that error appears in the above-identified patent and that said Letters Patent are hereby corrected as shown below:

Claim 5, line 1, should read:

5. The invention of claim 17 or 4 wherein said means re-

Claim 5, line 2, should read:

sponsive to the electrical resistance between said probe

Claim 6, line 1, should read:

6. The invention of claim 17 or 4, and further comprising:

Signed and Sealed this

Sixteenth Day of March 1982

[SEAL]

Attest:

GERALD J. MOSSINGHOFF

Attesting Officer     Commissioner of Patents and Trademarks